United States Patent
Yoshino

(10) Patent No.: US 11,348,676 B2
(45) Date of Patent: May 31, 2022

(54) MEDICAL EXAMINATION SYSTEM CONTROL APPARATUS AND CONTROL METHOD THEREFOR

(71) Applicant: CANON KABUSHIKI KAISHA, Tokyo (JP)

(72) Inventor: Hiroaki Yoshino, Yokohama (JP)

(73) Assignee: CANON KABUSHIKI KAISHA, Tokyo (JP)

(*) Notice: Subject to any disclaimer, the term of this patent is extended or adjusted under 35 U.S.C. 154(b) by 910 days.

(21) Appl. No.: 14/586,769

(22) Filed: Dec. 30, 2014

(65) Prior Publication Data

US 2015/0113463 A1   Apr. 23, 2015

Related U.S. Application Data

(62) Division of application No. 12/107,688, filed on Apr. 22, 2008, now abandoned.

(30) Foreign Application Priority Data

Apr. 25, 2007   (JP) .............................. JP2007-115636

(51) Int. Cl.
*A61B 6/00* (2006.01)
*G05B 15/02* (2006.01)
*G16H 30/40* (2018.01)
*G16H 80/00* (2018.01)
*A61B 5/055* (2006.01)
*A61B 8/00* (2006.01)
(Continued)

(52) U.S. Cl.
CPC .............. *G16H 30/20* (2018.01); *A61B 6/00* (2013.01); *A61B 6/5211* (2013.01); *A61B 6/542* (2013.01); *A61B 6/545* (2013.01); *A61B 6/563* (2013.01); *G05B 15/02* (2013.01); *G06F 3/04845* (2013.01); *G16H 30/40* (2018.01); *G16H 40/63* (2018.01); *G16H 80/00* (2018.01); *A61B 5/055* (2013.01); *A61B 8/00* (2013.01)

(58) Field of Classification Search
CPC ............. G06F 3/04845; G06F 19/3406; G06F 19/3425; G05B 15/02; G06Q 50/24; G16H 30/20; G16H 30/40; G16H 40/63; G16H 80/00; A61B 6/00; A61B 6/5211; A61B 6/542; A61B 6/545; A61B 6/563; A61B 5/055; A61B 8/00
USPC ....................................................... 705/2–3
See application file for complete search history.

(56) References Cited

U.S. PATENT DOCUMENTS

| 2003/0206646 A1* | 11/2003 | Brackett | G06F 19/321 |
| | | | 382/128 |
| 2006/0100912 A1* | 5/2006 | Kumar | G06F 16/951 |
| | | | 705/4 |

FOREIGN PATENT DOCUMENTS

EP   0687989 A2 *  12/1995  ........... G06F 19/322

* cited by examiner

Primary Examiner — Eliza A Lam
(74) Attorney, Agent, or Firm — Canon U.S.A., Inc. IP Division

(57) ABSTRACT

A medical examination system causes a display unit to display an object for shifting to examination processing together with patient information corresponding to identification information of a patient received by a receiving unit if the patient information of the patient is input via an operation unit when the receiving unit receives the identification information of the patient from an external device. The medical examination system shifts to the examination processing without causing the display unit to display the (Continued)

object if the patient information is not input via the operation unit when the receiving unit receives the patient information.

18 Claims, 15 Drawing Sheets

(51) Int. Cl.
*G16H 30/20* (2018.01)
*G16H 40/63* (2018.01)
*G06F 3/04845* (2022.01)

| PATIENT LIST | MANUAL INPUT | | | | | | | | | SYSTEM |

*3011* — PATIENT ID
*3012* — NAME
*3013* — COMMENT
*3014* — BIRTH DATE [ ] YEAR [ ] MONTH [ ] DAY

MALE | FEMALE | OTHERS
*3015*

*3005* —

| 1 | 2 | 3 | 4 | 5 | 6 | 7 | 8 | 9 | 0 |
| q | w | e | r | t | y | u | i | o | p |
| a | s | d | f | g | h | j | k | l | Home |
| Caps | z | x | c | v | b | n | m | . | End |

| TAB | | BS | < | > | NEXT |

FIG.10

| | INPUT VIA OPERATION AND DISPLAY UNIT 1005 | INPUT FROM UPSTREAM SYSTEM |
|---|---|---|
| DISPLAY DIALOG | ☐ | ☑ |
| PATIENT ID | ☐ | ☑ |
| NAME | ☐ | ☑ |
| BIRTH DATE | ☐ | ☑ |
| SEX | ☐ | ☑ |
| INPUT METHOD | ☐ | ☐ |

3080 — SETTING AS TO DISPLAY ITEM

PATIENT SPECIFYING FILE

0001

3051

MEDICAL EXAMINATION SYSTEM CONTROL APPARATUS AND CONTROL METHOD THEREFOR

CROSS-REFERENCE TO RELATED APPLICATIONS

This application is a Divisional of co-pending U.S. patent application Ser. No. 12/107,688 filed Apr. 22, 2008, which claims priority benefit of Japanese Patent Application No. 2007-115636 filed Apr. 25, 2007. The disclosures of the above-named applications are hereby incorporated by reference herein in their entirety.

BACKGROUND OF THE INVENTION

Field of the Invention

The present invention relates to a medical examination system for performing an examination by an X-ray imaging apparatus based on an input of patient information and a control method therefor.

Description of the Related Art

Recently, hospitals tend to construct a so-called hospital information system (HIS) for transmitting information among sections within each hospital. Also, each section in the hospital tries to construct an information system suitable for each section, for example, a radiation section constructs a radiology information system (RIS), and promotes on-line information transmission. In such information systems, not only an examination result recorded in a patient data base of a server can be referred to by retrieving that data through a terminal, but also examination request information from a doctor can be transmitted as an examination order to another undertaking section.

FIG. 17 illustrates an example of a network within a hospital. An HIS 1019 is an information system for connecting the sections via a network. The HIS 1019 has a server 1020. Sections 1021 and 1022 are, for example, an account section, a pharmaceutical section, or a medical examination section (an internal medicine section, a surgery section, an orthopedic surgery section, and the like). The sections 1021 and 1022 include HIS terminal 1023 and 1024 comprising a personal computer. An RIS 1010 is an information system within a radiation section. The RIS 1010 includes an RIS terminal 1011 comprising a gate way 1014 for connecting an image server 1013, the HIS 1019, and the RIS 1010 one another. The RIS 1010 also includes a personal computer provided in a radiation section 1012. In the RIS 1010 illustrated in FIG. 17, a photography room 1015 and a photography room 1016 are provided with an examination system 1017 and an examination system 1018, respectively.

When a subject which comes to an outpatient clinic goes through an outpatient reception, a doctor makes a diagnosis at each of the sections 1021 and 1022 of FIG. 17. At the time, it may be necessary for the subject to receive diagnosis at a plurality of sections. As a result of the diagnosis, if the doctor determines that, for example, an X-ray photography is necessary for the subject, the doctor inputs examination request information through the HIS terminal 1023, and the request information is transmitted to a radiation section 1012 that is an undertaking section. The request information instructed by the doctor is referred to as an examination order which includes information as to a name of a requesting section, and examination items such as "a region to be imaged: front of the chest, a side of the chest" in a case of the X-ray photography, a personal data of the patient, and the like. The radiation section 1012, upon receiving the examination order, transmits the order to proper examination systems 1017 or 1018 together with information as to an imaging condition.

For example, it is assumed that the section 1021 is a surgery section, the section 1022 is an orthopedic surgery section, and the examination system 1017 of the photography room 1015 is an X-ray examination system. When the subject goes through the outpatient reception and a doctor of the surgery section 1021 judges that X-ray photographs of the front of the chest and a side of the chest are necessary, the doctor inputs an examination order through the HIS terminal 1023. Thus, the input examination order is transmitted to the X-ray examination system 1017 in the photography room 1015 (Japanese Patent Application Laid-Open No. 2006-330815).

However, an input collision of examination orders may occur in the conventional method if an examination order is received from an upstream system (HIS system) while a user is operating the X-ray examination system. In such a case, it is difficult to determine which examination order should be accepted for imaging the X-ray photography.

In order to avoid the above-described circumstances, it is necessary for the system to have a switch operation that allows the user to select only one of the examination orders. However, in this case, the switching operation of the system may become complicated since the user is required to handle the switch operation.

SUMMARY OF THE INVENTION

The present invention is directed to an apparatus that is capable of readily determining whether the imaging is performed based on an examination order input by the user or based on an examination order from the upstream system.

According to an aspect of the present invention, a medical examination system of the present invention includes a receiving unit configured to receive identification information of a patient from an external device, an operation unit configured to input patient information about the patient, and a processing unit configured to cause a display unit to display an object for shifting to examination processing together with the patient information corresponding to the identification information of the patient received by the receiving unit if the patient information is input via the operation unit, and to execute the examination processing without causing the display unit to display the object if no patient information is input via the operation unit, when the receiving unit receives the identification information of the patient.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

FIG. 4 illustrates another example of a patient information input screen.

FIG. 10 illustrates an example of a setting method for patient information display items.

FIG. 11 illustrates an example in which patient information is input using a patient specifying file.

DETAILED DESCRIPTION OF THE EXEMPLARY EMBODIMENTS

Various exemplary embodiments, features, and aspects of the invention will be described in detail below with reference to the drawings.

First Exemplary Embodiment

Figure 1:
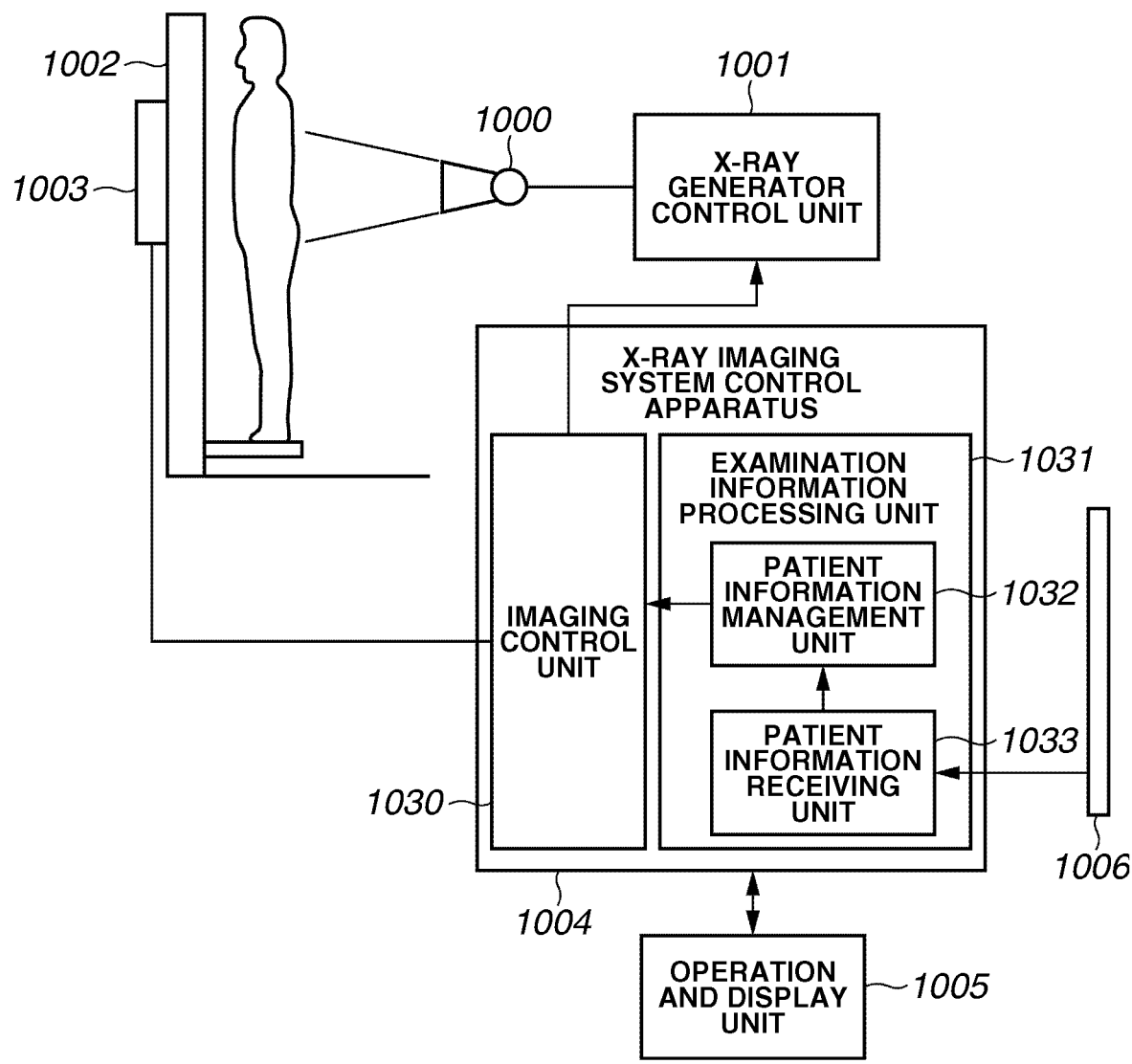
FIG. 1 illustrates an exemplary configuration of an X-ray imaging system according to an exemplary embodiment of the invention.

FIG. 1 illustrates an exemplary configuration of an X-ray imaging system of a medical examination system according to a first exemplary embodiment of the invention. The X-ray imaging system includes an X-ray tube bulb 1000 as an X-ray generator, an X-ray generator control unit 1001, a sensor unit 1002 including a sensor 1003, an X-ray imaging system control apparatus 1004, and an operation and display unit 1005.

The X-ray generator control unit 1001 is configured to control a high voltage application to the X-ray tube bulb 1000 based on information as to imaging conditions such as a tube current, a tube voltage, and an irradiation time from the X-ray imaging system control apparatus 1004 to control an X-ray generation.

The X-ray imaging system control apparatus 1004 processes a digital image signal obtained from the sensor 1003 and transmits various kinds of control information such as an imaging condition to the X-ray generator control unit 1001. The X-ray imaging system control apparatus 1004 includes, as a hardware, a read-only memory (ROM) as a computer readable storage medium for storing a software program and a RAM for expanding the software program stored in the ROM. The X-ray imaging system control apparatus 1004 further includes a central processing unit (CPU) for integrally controlling the entire system based on thus expanded software program.

The operation and display unit 1005 is a user interface for enabling the user to input patient information, retrieving/selecting a patient from a past patient list, shifting to an imaging mode, making various system settings, and the like. The operation and display unit 1005 includes a display, a mouse, and a keyboard.

Figure 17:
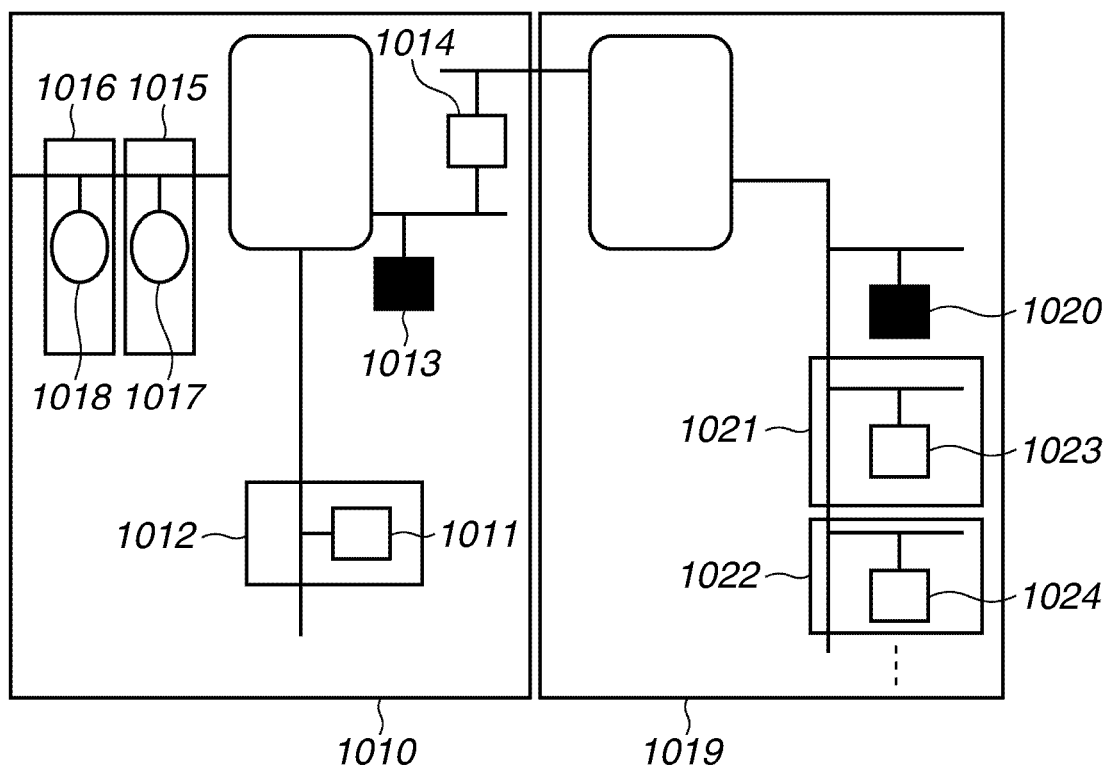
FIG. 17 illustrates a conventional configuration of an X-ray imaging system.

A network 1006 is connected to the HIS 1019 which is an external system in an upstream side as illustrated in FIG. 17. The X-ray imaging system illustrated in FIG. 1 receives an examination order from the HIS 1019 via the network 1006.

The operation information input by the user via the operation and display unit 1005 is detected by the X-ray imaging system control apparatus 1004. Then, a result of the process performed by the X-ray imaging system control apparatus 1004 is reflected on a display screen of the operation and display unit 1005.

For example, if a search keyword is input in the operation and display unit 1005, a patient information management unit 1032 retrieves the corresponding patient information unit 1032 from a storage device (not shown) which stores the patient information. Then, the result thereof is reflected in a patient list on the screen displayed in the operation and display unit 1005.

After the patient information is input via the operation and display unit 1005, the processing for shifting to imaging mode is executed and a patient information receiving unit 1033 assesses thus input patient information content. If there is no error in the input patient information content, the patient information management unit 1032 informs an imaging control unit 1030 as an imaging preparation that an imaging will be performed. The patient information management unit 1032 further notifies the operation and display unit 1005 of a shift to an imaging mode in order to change a display on the screen to that for imaging.

The X-ray imaging system control apparatus 1004 is realized by a computer. In the present embodiment, a transmission of the examination order is performed using a file system of the computer. For example, in the HIS 1019 (i.e., the external upstream system), a file including a patient ID corresponding to the examination order is generated in a prescribed folder. The patient ID is information for identifying a patient. The X-ray imaging system control apparatus 1004 periodically monitors a generation of a file. The patient information receiving unit 1033 receives the file as the examination order when the X-ray imaging system control apparatus 1004 detects the generation of the file. Then, the patient information management unit 1032 retrieves patient information corresponding to the patient ID from a storage device (not shown) based on the patient ID contained in the file.

When the patient information is specified after the patient information management unit 1032 normally retrieves the patient information, the processing for shifting to an imaging mode is executed. In a process of shifting to the imaging mode, the patient information management unit 1032 informs the imaging control unit 1030 that an imaging will be performed in order to make imaging preparations as well as notifies the operation and display unit 1005 of a change of a display in order to change a content displayed for the user.

At this stage, if an instruction is received from the HIS 1019 (i.e., the external upstream system) while the user is manually inputting the patient ID via the operation and display unit 1005, it is necessary to confirm to the user whether the imaging mode is to be executed. This is because, if the imaging mode is automatically executed, the input content corresponding to the patient ID which the user is manually inputting via the operation and display unit 1005 is scrapped or the input operation is temporarily interrupted. In the present embodiment, the imaging mode needs to be executed in response to an instruction of the user in order to avoid the above-described problems.

Figure 3:
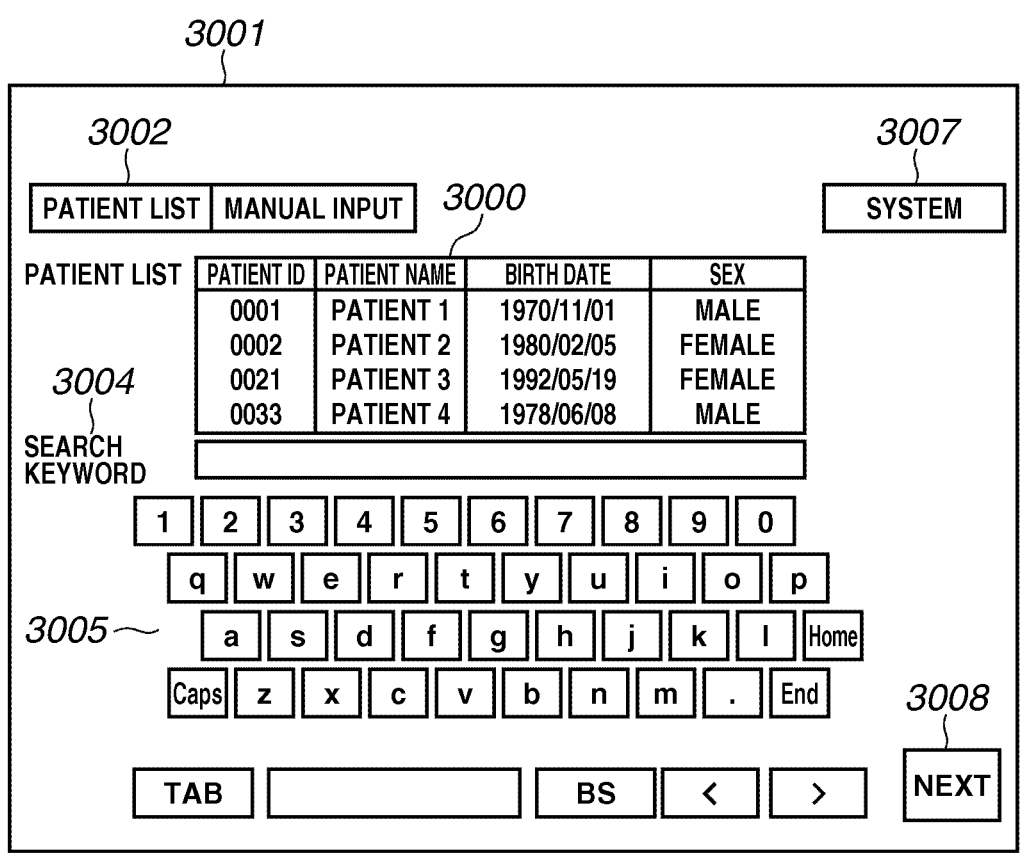
FIG. 3 illustrates an example of a patient information input screen.

FIG. 3 illustrates a screen 3001 displayed on a screen in the operation and display unit 1005 of the X-ray imaging system.

A patient selection can be made by selecting a patient from a patient list or directly inputting patient information. The screen includes at an upper part a selection button 3002 for switching between the above-described selection methods. A patient list 3000 is displayed at the center of the screen. The patient list 3000 is a list of patients that have been registered before. Below the patient list 3000, there is an area 3004 for inputting a search keyword, where a content input through a software keyboard 3005 is displayed.

The patient information management unit 1032 performs a forward matching search (prefix search) when the search keyword is input, and reflects the content to be displayed, on the patient list 3000. When the examination information processing unit 1031 detects that a patient is selected from the patient list and a "next" button 3006 is selected, the examination information processing unit 1031 causes the operation and display unit 1005 to display an imaging screen. When the examination information processing unit 1031 detects that the system button 3007 is selected, the display is shifted to a system setting screen to allow the user to change various settings.

FIG. 4 illustrates a manual entry screen 3010 of the patient information. Input items of the manual entry screen 3010 include a patient ID 3011, a patient name 3012, a comment 3013, a patient birth date 3014, and a patient sex 3015. The patient ID 3011, the patient name 3012, and the comment 3013 are input through a software keyboard at a bottom of the screen. When the examination information processing unit 1031 detects that a "next button" or a "system button" is selected, processing identical to what is illustrated in FIG. 3 is performed.

Figure 5:
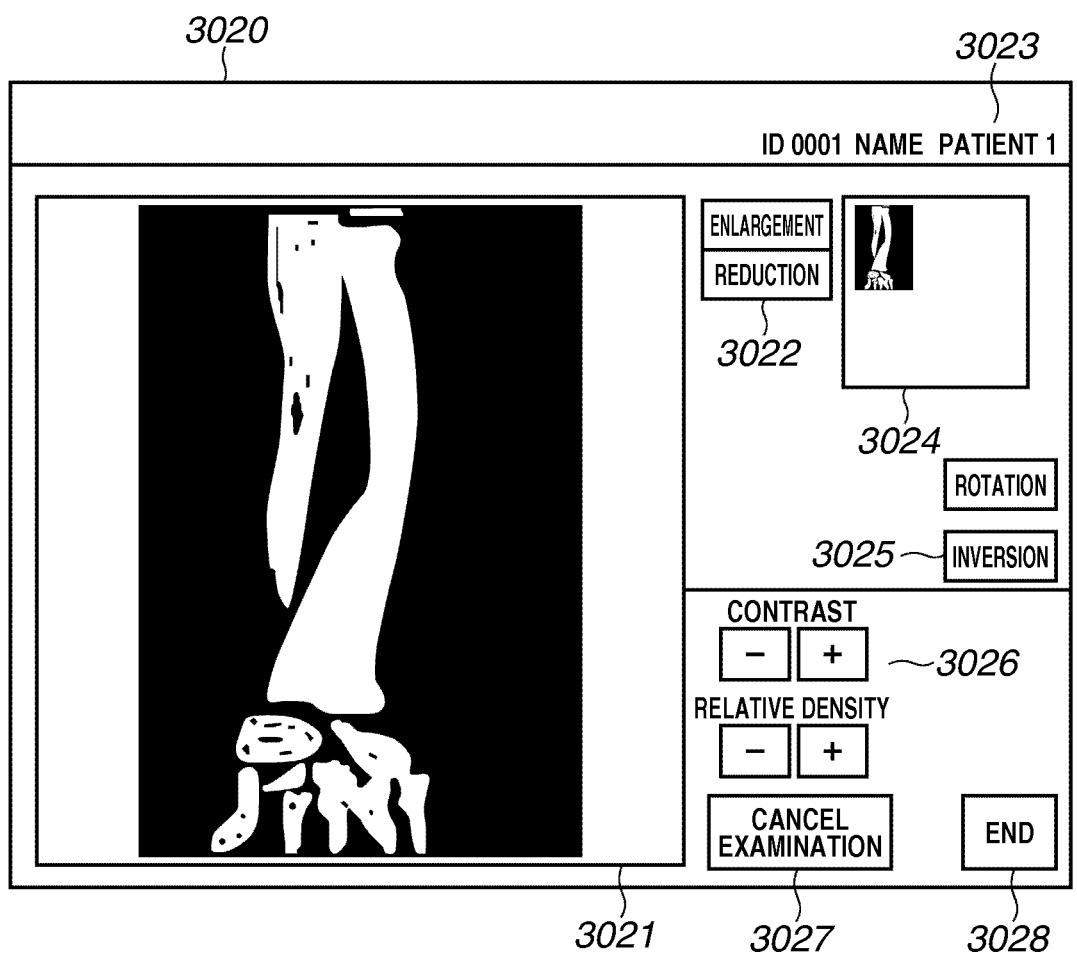
FIG. 5 illustrates an example of an imaging screen.

FIG. 5 illustrates an imaging screen 3020. A photographed image is displayed in an image display area 3021. The examination information processing unit 1031 executes an enlargement/reduction, a rotation, or an inversion of the displayed image according to a detected selection of the buttons 3022 and 3025. On upper section of the imaging screen 3020, patient information 3023 input in the patient information input screen is displayed. A thumbnail display area 3024 displays a reduced image of the photographed image. A button 3026 serves to change a contrast and a density of the displayed image. Buttons 3027 and 3028 serve to cancel or end imaging processing, respectively.

Figure 6:
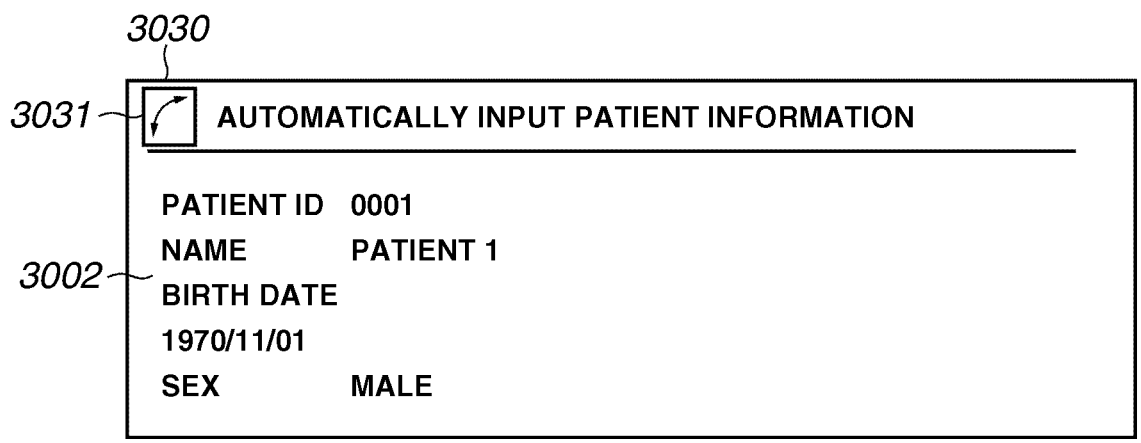
FIG. 6 illustrates an example of a confirmation screen of input patient information.

FIG. 6 illustrates a window 3030 which is displayed when the patient information is not input via the operation and display unit 1005 and the X-ray imaging system receives a file containing the patient ID from the HIS 1019 as the external upstream system. The window 3030 displays an icon 3031 indicating that the patient ID is input from the upstream system, the patient ID contained in the file, and patient information 3032 corresponding to the patient ID. After a specific time has lapsed, the window 3030 is closed and the imaging screen 3020 of FIG. 5 is displayed. The specific time can be optionally set. For instance, if the specific time period is set to zero second, the window 3030 itself will not be displayed on the screen.

Figure 7:
FIG. 7 illustrates another example of a confirmation screen of input patient information.

FIG. 7 is a window 3035 which is displayed when a file containing a patient ID is received from the HIS 1019 (i.e., the upstream system) while the user is inputting patient information via the operation and display unit 1005. In the window 3035, similar to the window 3030, an icon indicating that a patient ID is input from the upstream system, a patient ID contained in the file, and patient information corresponding to the patient ID are displayed.

The window 3035 illustrated in FIG. 7 differs from the window 3030 illustrated in FIG. 6 in that an OK button 3034 and a CANCEL button 3036 as selection objects are displayed in the window 3035. In the case where a file containing a patient ID is received from the upstream system 1007 while the user is inputting certain information in the manual entry screen 3010 of FIG. 4, if an imaging is performed without being treated, a content that the user has input in the manual entry screen 3010 will be scrapped or suspended. In FIG. 7, in the window 3035, the OK button 3034 and the CANCEL button 3036 are displayed as the selection objects in order to confirm if the content that the user is now inputting may be scrapped. The examination information processing unit 1031 closes the window 3035 upon detecting a selection of the OK button 3034 to display instead an imaging screen for performing examination processing. The examination information processing unit 1031 controls, upon detecting the selection of the CANCEL button 3036, the screen to return to the original manual entry screen without displaying the imaging screen based on the patient ID received from the upstream system.

Figure 8:
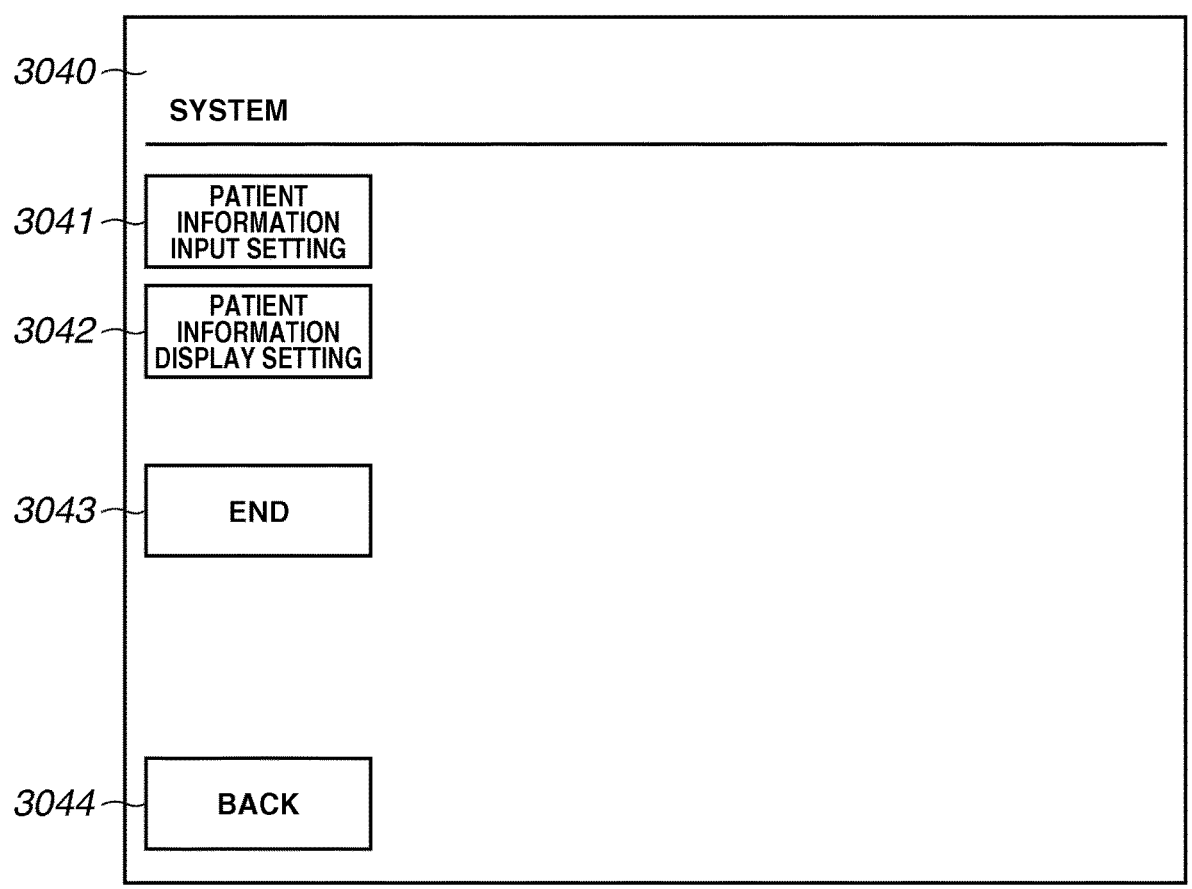
FIG. 8 illustrates an example of a setting method for a patient information input unit.

FIG. 8 illustrates a system screen 3040 for setting the X-ray imaging system. The system screen 3040 is displayed in association with a detection of a selection of the system button 3007 of FIG. 3. The system screen 3040 includes a patient information input setting button 3041, a patient information display setting button 3042, an end button 3043, and a BACK button 3044 for returning the screen to a patient information input screen. When the user selects the patient information input setting button 3041, he can perform a setting for inputting patient information from the upstream system. When the user selects the patient information display setting button 3042, the user can set items to be displayed for confirming the input content.

Figure 9:
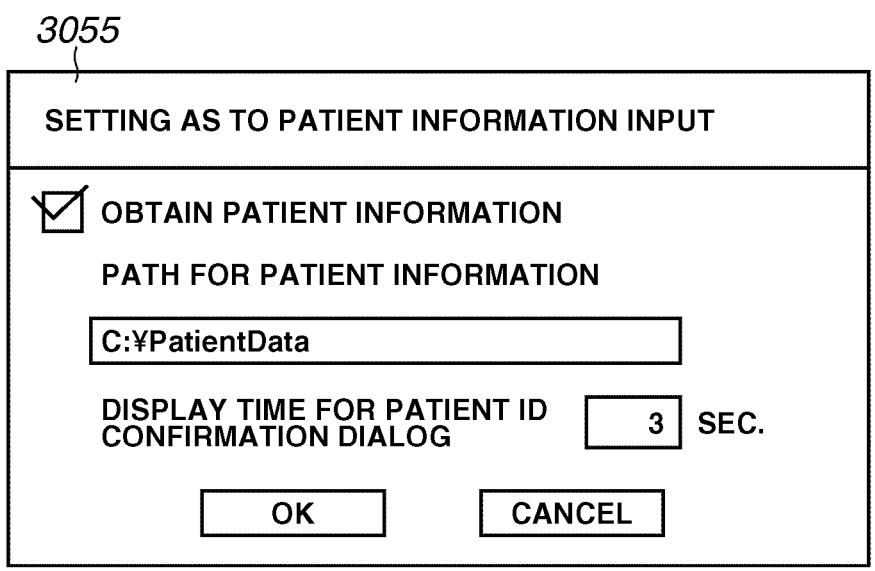
FIG. 9 illustrates another example of a setting method for a patient information input unit.

FIG. 9 illustrates a window 3055 for performing a setting for inputting patient information from the upstream system, which is displayed in response to a selection of the patient information input setting button 3041. In FIG. 9, the window 3055 can switch an able/disable function, set a password for the patient information, and set a display time of a patient ID confirmation window. The patient ID will be input from the upstream system only when an enabling setting is made in the window 3055. If the patient ID confirmation window display time is set to zero second, the window 3055 will not be displayed on the screen.

FIG. 10 illustrates a window 3080 for setting items of the patient information, which is displayed on the screen by the operation and display unit 1005 in response to a selection of the patient information display setting button 3042. The display items 3081 include a window, a patient ID, a patient name, a patient birth date, a patient sex, and an input method. The items to be displayed can be set optionally by checking a check box of each of the items. These items can be set for each input of the patient ID via the operation and display unit 1005 and the patient ID from the upstream system.

All the items will become invalid in association with unchecking of the check box in the window display. The "input method" of the display items is an item for identifying whether the patient information displayed on the screen corresponds to the input via the operation and display unit 1005 or to the input from the upstream system.

FIG. 11 illustrates a content contained in the patient specifying file identified by the patient ID. The patient specifying file contains only the patient ID 3051 in the form of a text data.

Figure 12:
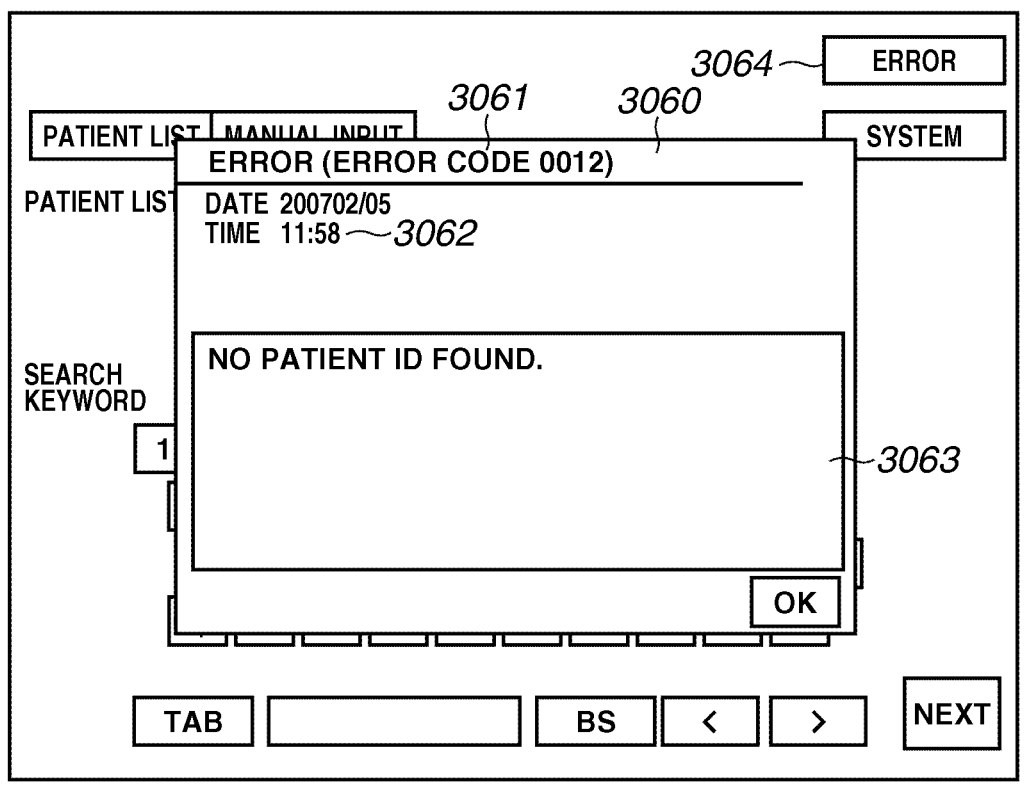
FIG. 12 illustrates an example of an error display when there is no specified patient information.

FIG. 12 illustrates a window 3060 to be displayed when the patient information corresponding to the patient ID specified by the upstream system is not included in the patient list stored in a storage device (not shown). The window 3060 includes an error code 3061, error information 3062, and an error content 3063. If there is no patient information corresponding to the patient ID in the patient list, an error button 3064 is displayed at an upper right section of the patient input screen 3001 of FIG. 3, and the window 3060 will be displayed when the error button 3064 is selected.

Figure 13:
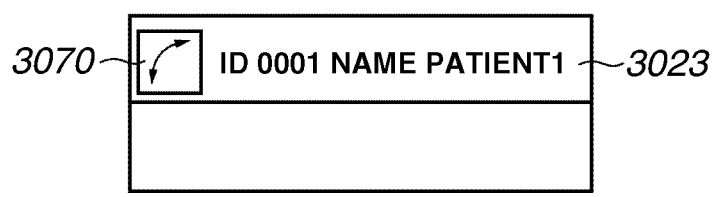
FIG. 13 illustrates an example of an input information display in an imaging screen.

FIG. 13 illustrates patient information 3023 to be displayed on an upper portion of an imaging screen 3020. In a case of imaging processing performed for the patient ID input from the upstream system, an icon 3070 indicating to that effect will be displayed on the screen.

Figure 2:
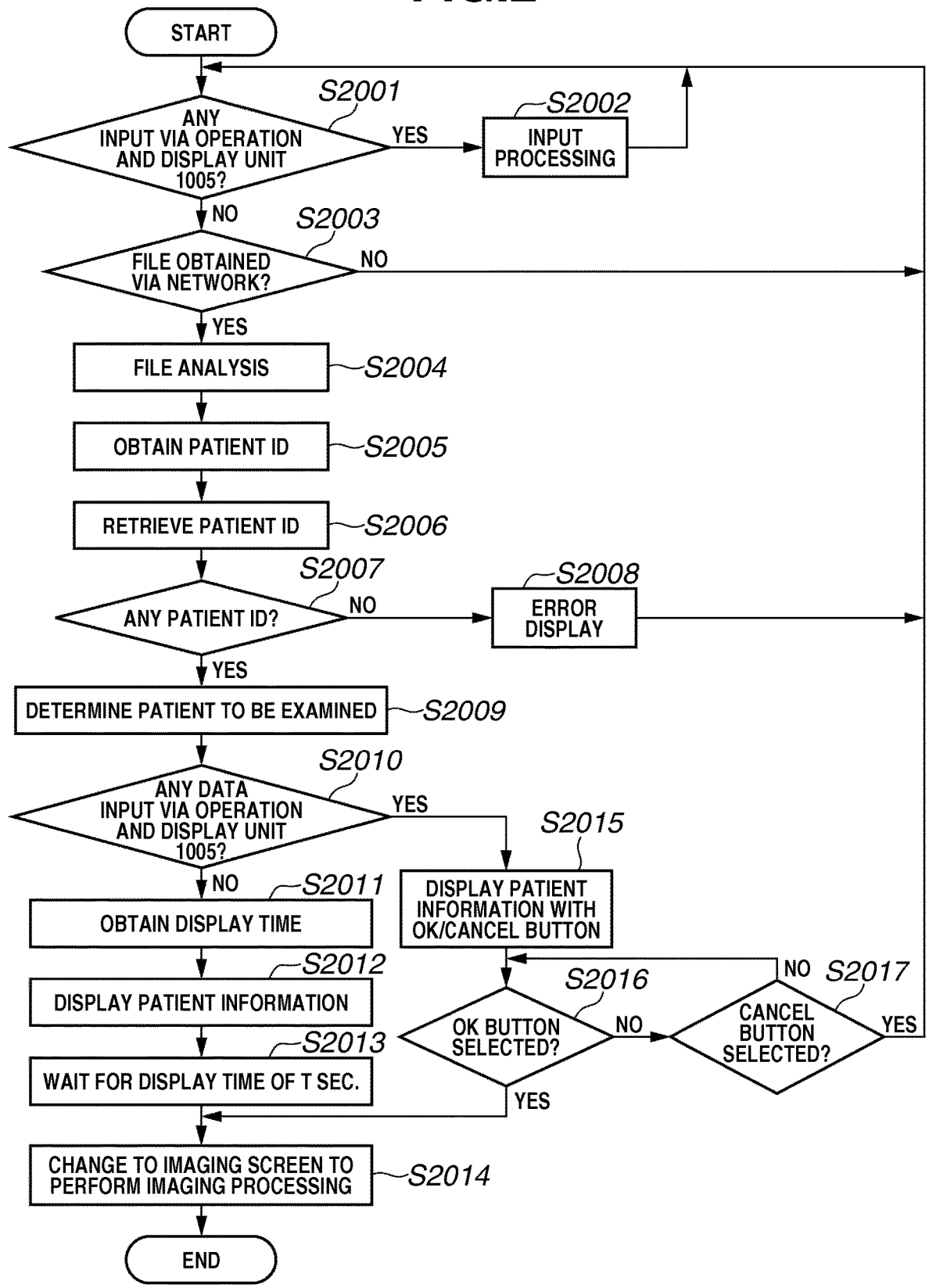
FIG. 2 is a flow chart illustrating processing steps of the X-ray imaging system according to a first exemplary embodiment of the invention.

FIG. 2 is a flow chart of the X-ray imaging system serving as a medical examination system. When the X-ray imaging system is activated, the patient information receiving unit 1033 checks whether the patient ID is input via the operation and display unit 1005 in step S2001. If there is an input of the patient ID (YES in step S2001), the patient information management unit 1032 performs processing corresponding to the patient ID in step S2002. The processing according to the input items in step S2002 includes a retrieval of past patient information, an execution of an imaging mode and a change of settings.

The patient information receiving unit 1033 subsequently checks whether it has obtained a file containing a patient ID generated in the HIS 1019 that is the upstream system via a network in step S2003.

If the file is received via a network, the patient information management unit 1032 performs an analysis of the file containing the patient ID in step S2004 to obtain the patient ID in step S2005.

Then, the patient information management unit 1032 retrieves the patient ID in order to confirm if the patient ID identical to the thus obtained patient ID is registered in the storage device (not shown) in step S2006.

The patient information management unit 1032 determines whether a patient ID identical to the obtained patient ID is registered in a storage device (not shown) in step S2007. If there is no corresponding patient ID found in the storage device (not shown)(NO in step S2007), in step S2008, the patient information management unit 1032 displays an error indicating that no corresponding patient ID was retrieved and returns the display screen to the original input standby condition.

When the patient information management unit 1032 retrieves the patient ID, it also obtains from the storage device information (not shown) such as patient name, patient sex, and patient birth date, which are related to the retrieved patient ID, to enter the thus obtained information as the information about an examination target patient in step S2009. Then, in step S2010, the patient information management unit 1032 determines whether the data is input via the operation display unit 1005.

The examination information processing unit 1031 determines that the data is now input if there is even one character input in any of the input items of the display screen such as a patient ID, a patient name, a patient birth date. The examination information processing unit 1031 determines that there is no input operation carried out if there is no character input in any of the input items. After the examination information processing unit 1031 determines that there is no input in any of the input items, it obtains information as to a display time for displaying the information of the patient on the screen in step S2011.

The display time is time for displaying the patient information relating to the analyzed patient ID. The patient information is displayed for confirmation if the HIS 1019 as the upstream system specifies the patient. The examination information processing unit 1031 controls the display of the information to disappear after a certain time period lapses. When the patient information is input via the operation and display unit 1005, the above processing will not be performed since the user himself is performing an input or a selection.

The examination information processing unit 1031 causes the operation and display unit 1005 to display the patient information throughout the thus obtained display time in step S2012. The examination information processing unit 1031 performs control that no other operation can be carried out via the operation and display unit 1005 until the display time lapses in step S2013. The examination information processing unit 1031 controls the operation and display unit 1005 to display an imaging screen after the display time has lapsed and notifies the imaging control unit 1030 to execute imaging processing in step S2014.

On the other hand, if it is determined that there is the data input via the operation and display unit 1005 in step S2010, the examination information processing unit 1031 displays a window 3035 for the patient information that includes the OK button 3034 and the CANCEL button 3036 of FIG. 7 in step S2015. The window 3035 will not be closed until selection of the OK button 3034 and the CANCEL button 3036 is detected.

The examination information processing unit 1031 detects that the OK button 3034 as an object for selection is selected in step S2016. Then, the examination information processing unit 1031 causes the operation and display unit 1005 to display the imaging screen in order to shift to the examination processing and notifies the imaging control unit 1030 to start the imaging processing in step S2014. When the examination information processing unit 1031 detects that the CANCEL button 3036 is selected in step S2017, an execution of the imaging processing corresponding to the patient ID from the HIS 1019 that is the upstream system is cancelled and the process returns to a standby state for inputting the patient information via the operation and display unit 1005.

As described above, when a file containing a patient ID is received via a network while the patient information is being input at a side of the X-ray imaging system, both of the OK button 3034 and the CANCEL button 3036 are displayed. Accordingly, the user can readily determine which input a priority should be given to. Owing to the above flow of processes, the present invention provides the X-ray imaging system that poses less burden to the user by changing contents in the confirmation windows depending on input states.

Figure 15:
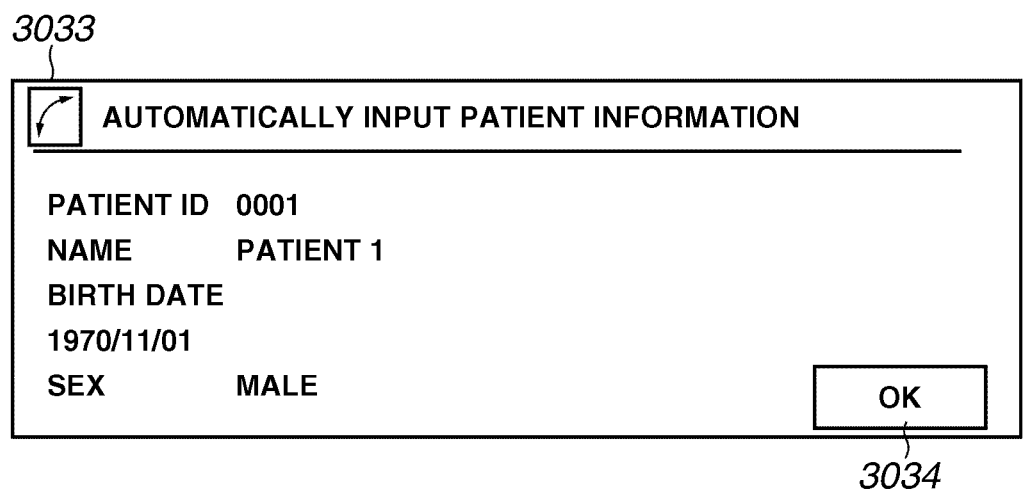
FIG. 15 illustrates an example of a confirmation screen of input patient information.

Similar to the window 3035 of FIG. 7, as a second exemplary embodiment, a window may display only OK button 3034 as illustrated in FIG. 15. FIG. 15 illustrates a window 3033 which displays patient information corresponding to a patient ID contained in a file received via a network from the upstream system. The window 3033 differs from the above-described window 3030 in that the window 3033 displays only the OK button 3034 as the object for selection. Upon detecting a selection of the OK button 3034, the screen displays the imaging screen 3020 of FIG. 5 from the window 3033.

Second Exemplary Embodiment

Figure 14:
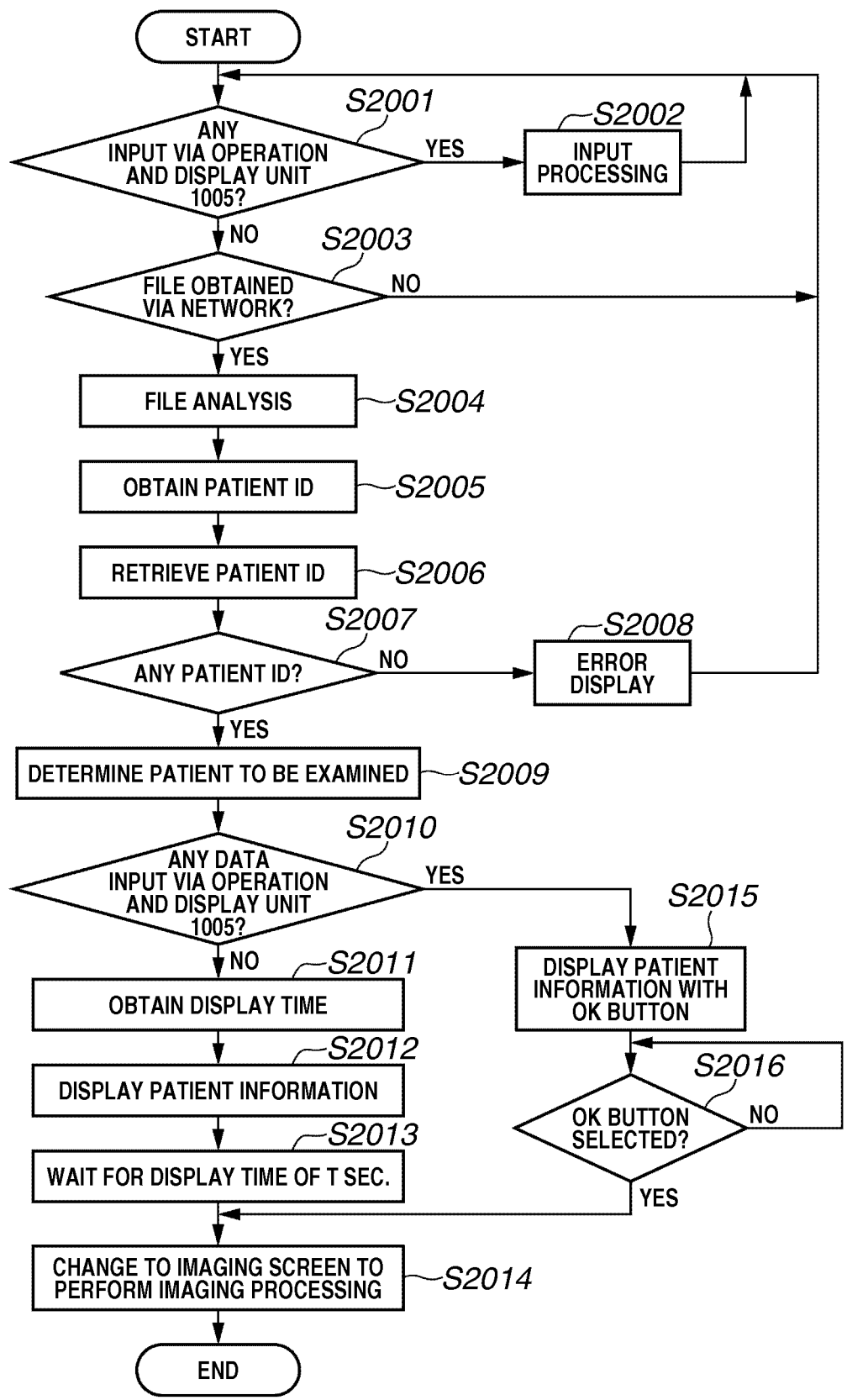
FIG. 14 is a flow chart illustrating processing steps of an X-ray imaging system according to a second exemplary embodiment of the invention.

FIG. 14 illustrates a flow chart of the X-ray imaging system for displaying a patient information window provided only with an OK button 3034. Description about steps represented by the same reference numbers as in FIG. 2 will be omitted since they will execute the similar processing as carried out in FIG. 2.

In the case where the examination information processing unit 1031 determines that there is data input via the operation and display unit 1005 when a file containing a patient ID is received via a network in step S2010 (YES in step S2010), the process proceeds to step S2015. In step S2015, the examination information processing unit 1031 causes the operation and display unit 1005 to display the window 3033 of the patient information provided with the OK button 3034 of FIG. 15. The window 3033 will not be closed until a selection of the OK button 3034 is detected.

The examination information processing unit 1031 detects a selection of the OK button 3034 in step S2016. The examination information processing unit 1031 then causes the operation and display unit 1005 to display an imaging screen in order to execute examination processing and notifies the imaging control unit 1030 to start imaging processing in step S2014.

As described above, the present invention can provide the X-ray imaging system that poses less burden to the user by seeking confirmation from the user only when required.

Third Exemplary Embodiment

According to a third exemplary embodiment, imaging processing corresponding to a patient ID contained in a file received from the upstream system via a network will be reserved when the patient information is input via the operation and display unit 1005.

Figure 16:
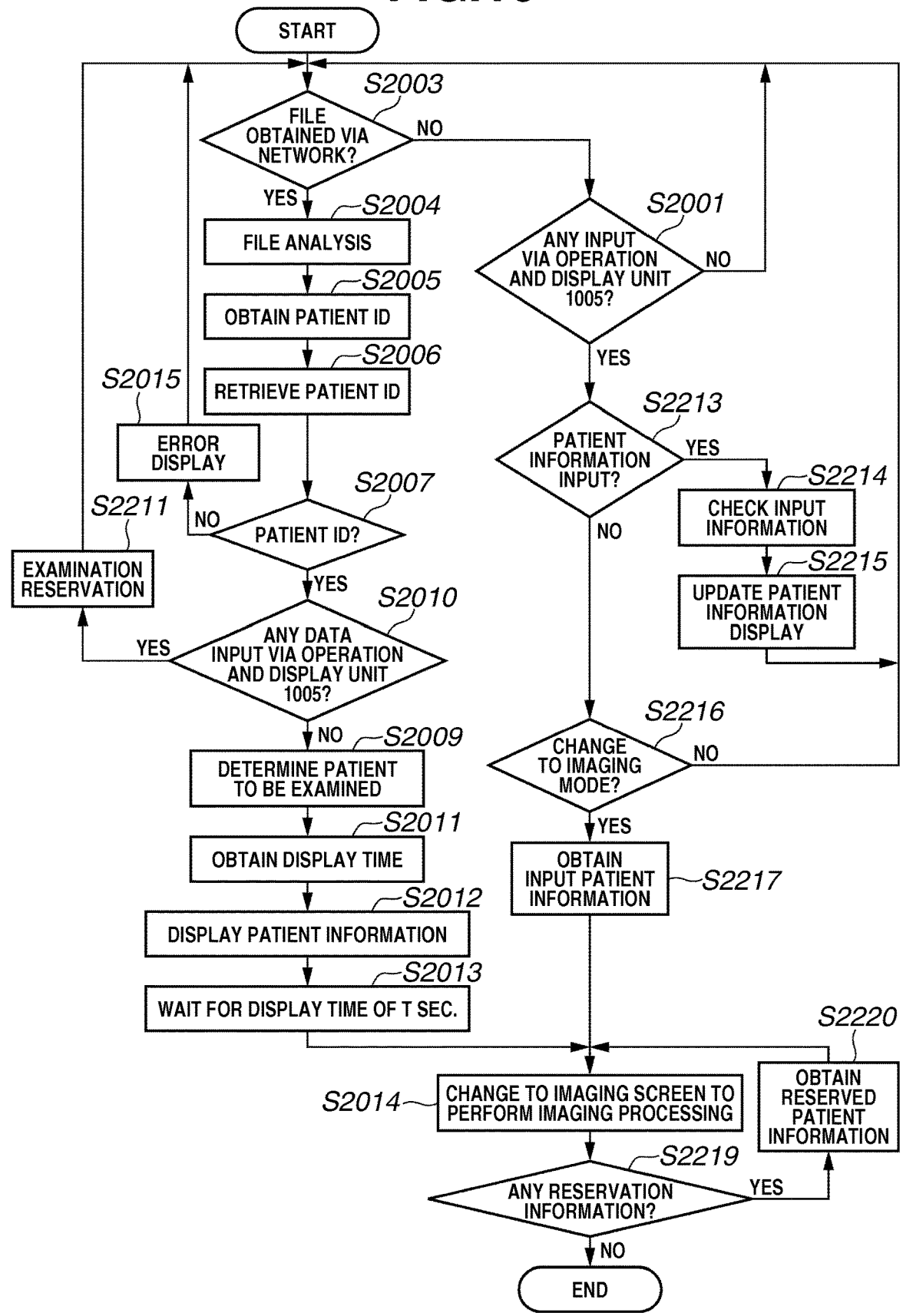
FIG. 16 is a flow chart illustrating processing steps of an X-ray imaging system according to a third exemplary embodiment of the invention.

FIG. 16 is a flow chart of the X-ray imaging system illustrating the third exemplary embodiment. Description about steps represented by the same reference numbers as illustrated in FIG. 2 will be omitted since they execute the same processing as carried out in FIG. 2.

In step S2010, if the examination information processing unit 1031 determines that there is patient information input via the operation and display unit 1005 when a file containing a patient ID is received via a network (YES in step S2010), the process proceeds to step S2211. Then, in step S2211, the patient information management unit 1032 causes a storage device (not shown) to register as examination reservation information the patient information corresponding to the patient ID contained in the file received via a network.

On the other hand, when the file containing the patient ID is not received via a network in step S2003 (NO in step S2003), the patient information receiving unit 1033 determines whether there is information input via the operation and display unit 1005.

The patient information receiving unit 1033 determines what was input when the information is input via the operation and display unit 1005. The patient information receiving unit 1033 initially determines whether the input is the patient information in step S2213.

The patient information management unit 1033 checks a maximum length of a character string, characters that can be entered and the like with regard to the input information in step S2214 if the input is the patient information. If no problem is found in the check, the examination information processing unit 1031 updates the patient information displayed on the operation and display unit 1005 in step S2215. Subsequently, the step goes back to the processing of step S2003.

On the other hand, when the patient information management unit 1033 determines that the input is not the patient information (NO in step S2213), it further determines whether the input is for executing an imaging processing in step S2216. If the input is for executing the imaging processing (YES in step S2216), in step S2217, the patient information management unit 1033 obtains thus input patient information via the operation and display unit 1005 as subject patient information.

The imaging control unit 1030 executes imaging processing corresponding to the thus obtained patient information in step S2014. If the imaging control unit 1030 notifies the patient information management unit 1032 of an end of the imaging processing, the patient information management unit 1032 confirms whether there is the patient information for which examination reservation is registered in the storage device (not shown) in step S2219. If there is the registered patient information, the patient information management unit 1032 obtains the thus registered patient information as information about the examination target patient in step S2220. Similarly, the imaging control unit 1030 executes imaging processing corresponding to the thus obtained patient information in step S2014.

As described above, according to the third exemplary embodiment, the patient information corresponding to the patient ID contained in the file received from the upstream system via a network is stored as an examination reservation. Accordingly, an examination can be carried out without obstructing an input operation performed by the user via the operation and display unit 1005. The examination of all input patients can be carried out according to the stored input content after the user finishes his input operation.

The above described third exemplary embodiment is a mere example and screen display items and file formats are not limited to the above described ones but can be modified as required.

For example, information such as "input received via a network" can be displayed on a display screen of the operation and display unit 1005 upon receiving a file from the upstream system via a network.

According to the present exemplary embodiment, the present invention is applied as an example to the X-ray imaging system as a medical examination system. However, the present invention is also applicable to a medical examination management system used for the other pathologic diagnosis such as a fundus photography system. In such a case, the imaging screen of FIG. 5 may be changed to the other graphical user interface (GUI).

The present invention can also be achieved by providing a storage medium which stores software (program code) for implementing functions of the above-described exemplary embodiments, to a system or an apparatus. The program code stored in the storage medium can be read and executed by a computer (central processing unit (CPU) or microprocessing unit (MPU)) of the system or the apparatus.

In this case, the software (program code) itself realizes the functions of the above-described exemplary embodiments. The software (program code) itself and the storage medium which stores the software (program code) constitute the present invention.

The storage medium can be, for example, a floppy disk, a hard disk, a magneto-optical disk, a compact disc-read-only memory (CD-ROM), a CD-recordable (CD-R), a CD-rewritable (CD-RW), a digital versatile disc (DVD)-ROM, a DVD-RAM, a DVD-RW, a DVD+RW, a magnetic tape, a nonvolatile memory card, or a ROM. Further, such software (program code) can be downloaded via a network.

Furthermore, the above-described exemplary embodiments can be not only realized by executing software (program code) read by a CPU. An operating system (OS) or the like working on a computer can also perform a part or the whole of processes according to instructions of the software (program code) and realize functions of the above-described exemplary embodiments.

Furthermore, software (program code) read from a storage medium can be stored in a memory equipped in a function expansion board inserted in a computer or a function expansion unit connected to a computer, and a CPU in the function expansion board or the function expansion unit can execute all or a part of the processing based on the instructions of the software (program code) to realize the functions of the above-described exemplary embodiments.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

What is claimed is:

1. A control apparatus for medical imaging, the control apparatus comprising:
   a receiver configured to receive first information of a first order of first medical imaging processing from an external apparatus;
   a memory storing a program; and
   one or more processors which, by executing the program, function as:
      a display control unit configured to, in a case where the first information is received by the receiver while the user is inputting second information of a second order of second medical imaging processing on an input screen for inputting information, cause a display unit to display an item for receiving an input from an operation unit, wherein the second information is independent from the first information, and the input is used to perform a determination of whether or not to display an imaging screen for performing the first medical imaging processing, wherein the imaging screen is different from the input screen, and
      a processing unit configured to, based on the determination, perform a the first medical imaging processing, corresponding to the first information or perform the second medical imaging processing corresponding to the second information,
   wherein the display control unit causes the display unit to display a window which is displayed when the first information is received from the external apparatus and selection objects to select if the second information is to be discarded, the selection objects being the item for receiving the input from the operation unit,
   wherein the processing unit performs the first medical imaging processing corresponding to the first information upon operation of the selection objects to discard the second information,
   wherein the receiver receives identification information of an object to be imaged as the first information, and
   wherein a patient identifier (ID) contained in the first information and patient information corresponding to the patient ID are displayed in the window.

2. The control apparatus of claim 1, wherein, in another case that the receiver receives the first information and the imaging screen is not displayed, the display control unit causes the display unit to, in response to a receipt of the first information by the receiver, display the imaging screen.

3. The control apparatus of claim 2, wherein, in the another case, the display control unit is configured to cause the display unit to, in response to a receipt of the first information by the receiver, display the received first information and the imaging screen.

4. The control apparatus of claim 3,
   wherein, in the another case, the display control unit is configured to cause the display unit to, in response to the receipt of the first information by the receiver, display the received first information, and
   wherein, after a predetermined period of time has passed since a start of a display of the received first information, the display control unit causes the display unit to display the imaging screen.

5. The control apparatus of claim 1, wherein, if the display control unit determines, based on the input from the operation unit, to display the imaging screen, the display control unit causes the display unit to display the imaging screen in response to the determination.

6. The control apparatus of claim 1, wherein, if the display control unit determines, based on the input from the operation unit, not to display the imaging screen, the display control unit causes the display unit to display a screen for inputting information of the second medical imaging processing.

7. The control apparatus of claim 1, wherein, if the display control unit determines, based on the input from the operation unit, to display the imaging screen, the display control unit deletes the input second information.

8. The control apparatus of claim 1, wherein, if the display control unit determines, based on the input from the operation unit, not to display the imaging screen, the display control unit performs a process for registering the first order as an examination reservation.

9. The control apparatus of claim 1, wherein the receiver receives the first information from a hospital information system.

10. The control apparatus of claim 1, wherein the second information is information for a second order of medical imaging processing, the second order being different from the first order.

11. The control apparatus of claim 1, wherein the display control unit is configured to determine whether or not the receiver receives the first information during a time period from a first time when input for obtaining information of an object to be imaged is started to a second time when the information of the object to be imaged is specified by the operation unit.

12. A control apparatus for medical imaging, the apparatus comprising:
a receiver configured to receive first information of a first order of medical imaging processing from an external apparatus;
a memory storing a program; and
one or more processors which, by executing the program function as:
a processing unit configured to, in a first case that a screen for inputting information of medical imaging processing is displayed on a display unit and the first information is received by the receiver while the user is inputting second information of a second order of second medical imaging processing on an input screen for inputting information, determine whether to start the first medical imaging processing corresponding to the received first information or to perform a process for registering the first order as an examination reservation,
wherein, in a second case that the receiver receives the first information and the screen is not displayed, the processing unit is configured to
determine to perform a process for starting the first medical imaging processing corresponding to the received first information, in response to a receipt of the first information by the receiver; and
perform the first medical imaging processing corresponding to the received first information and the second medical imaging processing corresponding to the input second information, and
wherein the processing unit causes the display unit to display a window which is displayed when the first information is received from the external apparatus and selection objects to select if the second information is to be discarded,
wherein the processing unit performs the first medical imaging processing corresponding to the first information upon operation of the selection objects to discard the second information,
wherein the receiver receives identification information of an object to be imaged as the first information, and
wherein a patient identifier (ID) contained in the first information and patient information corresponding to the patient ID are displayed in the window.

13. A control apparatus for medical imaging, the apparatus comprising:
a receiving unit configured to receive first information of a first order of medical imaging processing from an external apparatus;
a memory storing a program; and
one or more processors which, by executing the program function as:
a display control unit configured to cause a display unit to, in a case where the first information is received while the user is inputting second information of a second order of second medical imaging processing on an input screen for inputting information, cause the display unit to display an item for receiving an input from an operation unit to determine whether or not to display an imaging screen for performing first medical imaging processing, wherein the imaging screen is different from the input screen; and
a processing unit configured to perform the first medical imaging processing corresponding to the first information with the imaging screen displayed in response to the input from the operation unit or the second medical imaging processing corresponding to the second information,
wherein the display control unit causes the display unit to display a window which is displayed when the first information is received from the external apparatus and selection objects to select if the second information is to be discarded, the selection objects being the item for receiving the input from the operation unit,
wherein the processing unit performs the first medical imaging processing corresponding to the first information upon operation of the selection objects to discard the second information,
wherein the receiver receives identification information of an object to be imaged as the first information, and
wherein a patient identifier (ID) contained in the first information and patient information corresponding to the patient ID are displayed in the window.

14. The imaging apparatus of claim 13, further comprising an X-ray generator.

15. A system for medical imaging, comprising:
a receiver configured to receive first information of a first order of medical processing from an external apparatus;
a memory storing a program; and
one or more processors which, by executing the program, function as:
a display control unit configured to, in a case that a screen for inputting information of medical imaging is displayed on a display unit and the first information is received by the receiver while the user is inputting second information of a second order of second medical imaging processing on a screen for inputting information, cause a display unit to display an item for receiving an input from an operation unit to determine whether or not to display an imaging screen for performing first medical imaging processing corresponding to the first information, and
a processing unit configured to perform the first medical imaging processing corresponding to the first information with the imaging screen displayed in response to the input from the operation unit and the second medical imaging processing corresponding to the second information,
wherein the display control causes the display unit to display a window which is displayed when the first information is received from the external apparatus and selection objects to select if the second information is to be discarded, the selection objects being the item for receiving the input from the operation unit,
wherein the processing unit performs the process of the first medical imaging processing corresponding to the first information upon operation of the selection objects to discard the second information,
wherein the receiver receives identification information of an object to be imaged as the first information, and
wherein a patient identifier (ID) contained in the first information and patient information corresponding to the patient ID are displayed in the window.

16. A method of controlling medical imaging, comprising:
receiving, at a receiver, first information of a first order of first medical imaging processing from an external apparatus;
controlling a display unit to, in a case where the first information is received by the receiver while the user is inputting second information of a second order of second medical imaging processing on an input screen for inputting information, display an item for receiving an input from an operation unit, wherein the second information is independent from the first information, and the input is used to perform a determination of whether or not to display an imaging screen for performing first medical imaging processing; and performing, based on the determination, a process of the first medical imaging processing corresponding to the first information or a process of second medical imaging processing corresponding to the second information, wherein the controlling causes the display unit to display a window which is displayed when the first information is received from the external apparatus and selection objects to select if the second information is to be discarded, the selection objects being the item for receiving the input from the operation unit, wherein the performing includes performing the process of the first medical imaging processing corresponding to the first information upon operation of the selection objects to discard the second information, wherein the receiver receives identification information of an object to be imaged as the first information, and wherein a patient identifier (ID) contained in the first information and patient information corresponding to the patient ID are displayed in the window.

17. A control method for medical imaging, comprising:

receiving, at a receiver, first information of a first order of first medical imaging processing from an external apparatus;

determining, in a first case that a screen for inputting information of medical imaging processing is displayed on a display unit and second information independent of the first order has already been input via the screen before the receiver receives the first information from the external apparatus, whether to perform a process for starting the first medical imaging processing corresponding to the first information or to perform a process for registering the first order as an examination reservation, determining, in a second case that the receiver receives the first information and the screen is not displayed, to perform a process for starting the first medical imaging processing corresponding to the received first information, in response to a receipt of the first information by the receiver; and performing a process of the first medical imaging processing corresponding to the received first information and the second medical imaging processing corresponding to the input second information, wherein the display unit displays a window which is displayed when the first information is received from the external apparatus and selection objects to select if the second information is to be discarded, and wherein the performing includes performing the first medical imaging processing corresponding to the received first information upon operation of the selection objects to discard the second information, wherein the receiver receives identification information of an object to be imaged as the first information, and wherein a patient identifier (ID) contained in the first information and patient information corresponding to the patient ID are displayed in the window.

18. An apparatus for controlling medical imaging, the apparatus comprising:

a networking port configured to receive a first order for medical imaging processing from an external apparatus;

a display unit configured to display a manual input screen for receiving a second order for medical imaging processing from a user, and to display an imaging screen for showing a medical imaging process;

a memory storing a program; and one or more processors which, by executing the program, is configured to determine whether to perform first medical imaging processing based on a reception from the external apparatus via the networking port or to perform second medical imaging processing based on an input from the user via the manual input screen, wherein, in a case where the networking port receives the first order for the first medical imaging processing from the external apparatus at a same time as the user inputs the second order for the second medical imaging processing via the manual input screen, the display unit displays a selection item for allowing the user to select whether to process the first order or the second order, wherein, based on a selection made by the user, the processor is configured to perform the first medical imaging processing and cause the display unit to display the imaging screen, or perform the second medical imaging processing without displaying the imaging screen, wherein the processor causes the display unit to display a window which is displayed when the first order is received from the external apparatus and selection objects to confirm if the second order is to be discarded, the selection objects being the selection item for allowing the user to select, wherein the processor performs the first medical imaging processing corresponding to the first order upon operation of the selection objects to discard the second information, wherein the receiver receives identification information of an object to be imaged as the first information, and wherein a patient identifier (ID) contained in the first information and patient information corresponding to the patient ID are displayed in the window.

* * * * *